United States Patent [19]

Berg

[11] Patent Number: 5,380,405
[45] Date of Patent: Jan. 10, 1995

[54] SEPARATION OF ALPHA-PHELLANDRENE FROM 3-CARENE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 184,918

[22] Filed: Jan. 24, 1994

[51] Int. Cl.6 ............................ B01D 3/36; C07C 7/06
[52] U.S. Cl. ........................................ 203/57; 203/60; 203/62; 203/63; 585/350; 585/860; 585/862; 585/864; 585/866
[58] Field of Search ................. 203/63, 60, 57, 62; 585/864, 866, 862, 860, 355, 350; 512/5

[56] References Cited

U.S. PATENT DOCUMENTS

| | | | |
|---|---|---|---|
| 2,459,433 | 1/1949 | Johnson et al. | 203/65 |
| 2,818,435 | 12/1957 | Bain et al. | 585/355 |
| 3,422,029 | 1/1969 | Booth | 585/355 |
| 3,987,121 | 10/1976 | Koppel et al. | 203/64 |
| 4,136,126 | 1/1979 | Hirschy et al. | 585/355 |

*Primary Examiner*—Wilbur Bascomb, Jr.

[57] ABSTRACT alpha-Phellandrene is difficult to separate from 3-carene by conventional distillation or rectification because of the proximity of their boiling points. alpha-phellandrene can be readily separated from 3-carene by azeotropic distillation. Effective agents are methyl formate, nitroethane and acetal.

2 Claims, No Drawings

SEPARATION OF ALPHA-PHELLANDRENE FROM 3-CARENE BY AZEOTROPIC DISTILLATION

FIELD OF THE INVENTION

This invention relates to a method for separating alpha-phellandrene from 3-carene using certain organic liquids as the agent in azeotropic distillation.

DESCRIPTION OF PRIOR ART

Azeotropic distillation is the method of separating close boiling compounds or azetropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

There are a number of commercial processes which produce complex mixtures of hydrocarbons and oxygenated organic compounds, e.g. turpentine separation. Two of the commonest close boiling compounds in this mixture are alpha-phellandrene and 3-carene. alpha-Phellandrene boils at 175° C. and 3-carene at 167° C. The relative volatility between these two is 1.05 which makes it very difficult to separate them by conventional rectification. Azeotropic distillation would be an attractive method of affecting the separation of alpha-phellandrene from 3-carene if agents can be found that (1) will create a large apparent relative volatility between alpha-phellandrene and 3-carene and (2) are easy to recover from alpha-phellandrene. Table 1 shows the relative volatility required to obtain 99% purity. With no agent, the relative volatility is 1.05 and 253 actual plates are required. With an agent giving a relative volatility of 2.0, only nineteen plates are required.

OBJECTIVE OF THE INVENTION

The object of this invention is to provide a process or method of azeotropic distillation that will enhance the relative volatility of alpha-phellandrene from 3-carene in their separation in a rectification column. It is a further object of this invention to identify organic compounds which in addition to the above constraints, are stable, can be separated from alpha-phellandrene and recyled to the azeotrope column with little decomposition.

TABLE 1

Theoretical and Actual Plates Required vs. Relative Volatility for alpha-Phellandrene - 3-Carene Separation

| Relative Volatility | Theoretical Plates Required At Total Reflux, 99% Purity | Actual Plates Required, 75% Efficiency |
|---|---|---|
| 1.05 | 190 | 253 |
| 1.2 | 51 | 68 |
| 1.5 | 22 | 29 |
| 2.0 | 14 | 19 |

SUMMARY OF THE INVENTION

The objects of this invention are provided by a process for separating alpha-phellandrene from 3-carene which entails the use of certain organic compounds as the agent in azeotropic distillation.

DETAILED DESCRIPTION OF THE INVENTION

TABLE 2

Effective Azeotropic Distillation Agents For Separating alpha-Phellandrene From 3-Carene

| Compounds | Relative Volatility |
|---|---|
| None | 1.05 |
| Methyl t-butyl ether | 1.2 |
| Methyl formate | 1.7 |
| Methyl caproate | 2.7 |
| Amyl acetate | 1.9 |
| Methyl amyl acetate | 1.85 |
| Acetonitrile | 1.3* |
| Methyl acetate | 1.2* |
| Ethyl acetate | 1.25* |
| Propyl formate | 1.2* |
| Dimethylformamide | 1.3* |
| Nitromethane | 1.3* |
| Nitroethane | 1.5* |
| Acetal | 2.0* |

*Brings 3-carene out as overhead product.

I have discovered that certain organic compounds will greatly improve the relative volatility of alpha-phellandrene to 3-carene and permit the separation of alpha-phellandrene from 3-carene by rectification when employed as the agent in azeotropic distillation. Table 2 lists the compounds that I have found to be effective. They are methyl t-butyl ether, methyl formate, methyl caproate, amyl acetate, methyl amyl acetate, acetonitrile, methyl acetate, ethyl acetate, propyl formate, dimethylformamide, nitromethane, nitroethane and acetal.

THE USEFULNESS OF THE INVENTION

The usefulness or utility of the invention can be demonstrated by referring to the data presented in Tables 1 and 2. All of the successful agents show that alpha-phellandrene can be separated from 3-carene by means of azeotropic distillation in a rectification column and that the ease of separation as measured by relative volatility is considerable.

WORKING EXAMPLES

Example 1

Eighty grams of alpha-phellandrene, 20 grams of 3-carene and 50 grams of methyl caproate were charged to a vapor-equilibrium still and refluxed for twelve hours. Analysis indicated a vapor composition of 82.8% alpha-phellandrene, 17.2% 3-carene; a liquid composition of 63.4% alpha-phellandrene, 36.6% 3-carene which is a relative volatility of 2.7.

Example 2

Sixty grams of alpha-phellandrene, 40 grams of 3-carene and 120 grams of methyl amyl acetate were placed in the stillpot of a 7.3 theoretical plate glass perforated plate rectification column and refluxed for three hours. The overhead composition was 87.5% alpha-phellandrene, 12.5% 3-carene; the bottoms composition was 7.1% alpha-phellandrene, 92.9% 3-carene. This is a relative volatlity of 1.85.

Example 3

Thirty grams of 3-carene, 70 grams of alpha-phellandrene and 50 grams of acetal were charged to a vapor-liquid equilibrium still and refluxed for four hours. Analysis indicated a vapor composition of 36.3% 3-carene, 63.7% alpha-phellandrene; a liquid composition of 22.1% 3-carene, 77.9% alpha-phellandrene which is a relative volatility of 2.0.

I claim:

1. A method for recovering alpha-phellandrene from a mixture of alpha-phellandrene and 3- carene which comprises distilling a mixture of alpha-phellandrene and 3-carene in the presence of an azeotrope forming agent, recovering the alpha-phellandrene and the azeotrope forming agent as overhead product and obtaining the 3-carene as bottoms product, wherein said azeotrope forming agent consists of one material selected from the group consisting of methyl t-butyl ether, methyl formate, methyl caproate, amyl acetate and methyl amyl acetate.

2. A method for recovering 3-carene from a mixture of 3-carene and alpha-phellandrene which comprises distilling a mixture of 3-carene and alpha-phellandrene in the presence of an azeotrope forming agent, recovering the 3-carene and the azeotrope forming agent as overhead and obtaining the alpha-phellandrene as bottoms product, wherein said azeotrope forming agent consists of one material selected from the group consisting of acetonitrile, methyl acetate, ethyl acetate, propyl formate, dimethylformamide, nitromethane, nitroethane and acetal.

* * * * *